Figure 4:
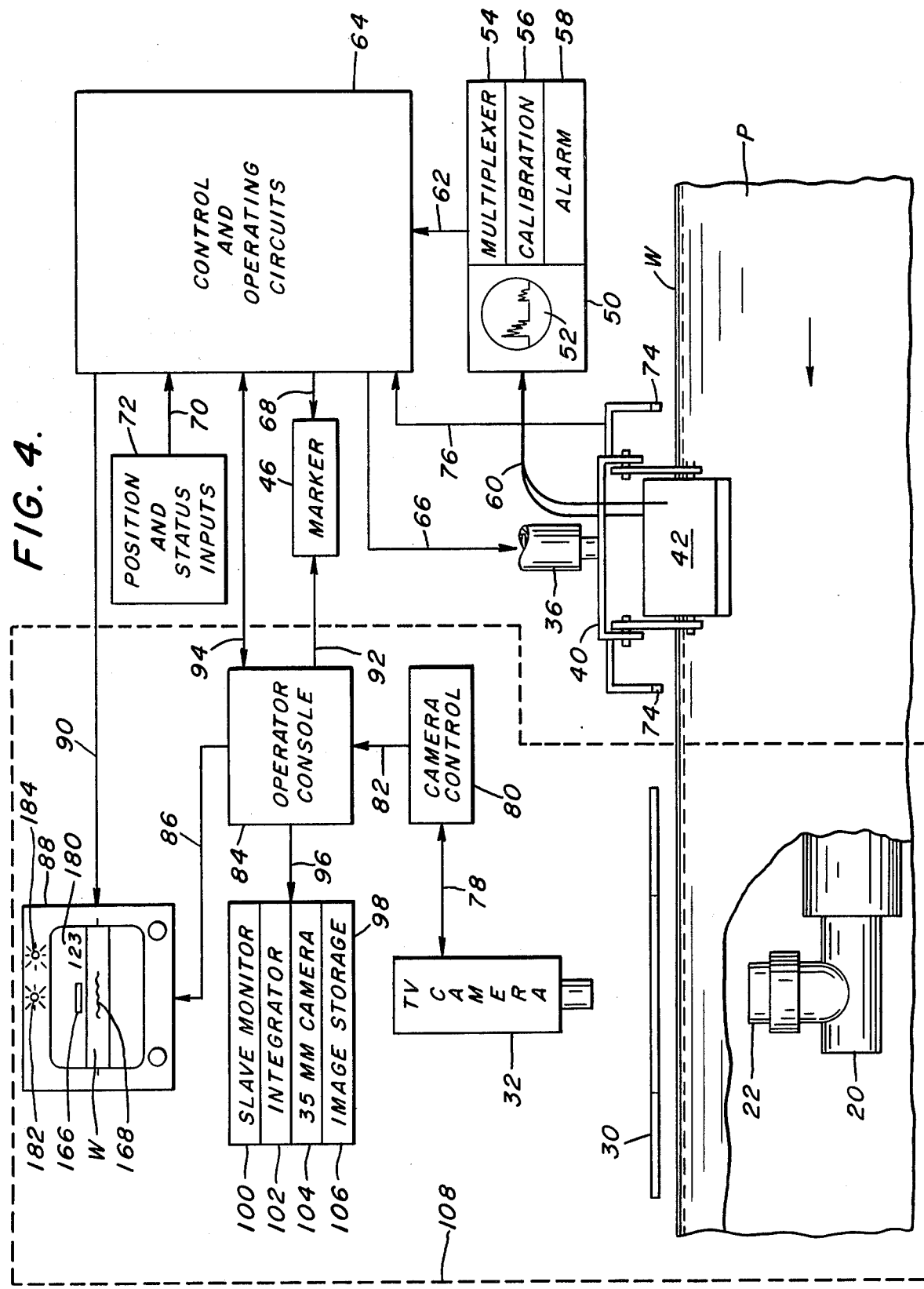

United States Patent [19]

Henry, Jr. et al.

[11] 4,055,989
[45] Nov. 1, 1977

[54] WELD INSPECTION SYSTEM WITH DUAL FLAW DETECTION

[75] Inventors: Edwin Blair Henry, Jr., Mount Lebanon Township, Allegheny County; John A. Patsey, Penn Hills Township, Allegheny County; Ralph G. Rudolph, Edgewood Borough; Donald G. Schindler, Whitehall Borough, all of Pa.

[73] Assignee: United States Steel Corporation, Pittsburgh, Pa.

[21] Appl. No.: 667,763

[22] Filed: Mar. 17, 1976

[51] Int. Cl.² .......................................... G01N 29/04
[52] U.S. Cl. ...................................... 73/588; 73/592; 73/619; 73/621; 73/622; 73/637; 73/638
[58] Field of Search ................... 73/67.5 R, 67.6, 67.7, 73/67.8 R, 67.8 S; 250/312, 358 P

[56] References Cited
U.S. PATENT DOCUMENTS 3,448,606  6/1969  Flaherty et al. .................. 73/67.8 S
3,686,932  8/1972  Ries et al. ......................... 73/67.5 R

OTHER PUBLICATIONS

Barkow, A. G., NDT Applied to Pipeline Construction and Operation in the U.S.A. from Materials Evaluation, Apr. 1967, pp. 65, 72.

*Primary Examiner*—Jerry W. Myracle
*Attorney, Agent, or Firm*—Rea C. Helm

[57] ABSTRACT

A weld inspection system uses fluoroscopic flaw detection particularly sensitive to volumetric type weld flaws and ultrasonic flaw detection particularly sensitive to planar type weld flaws. Both inspections are performed simultaneously throughout the pipe length. Each system marks the pipe with a distinguishing mark to identify the location of the flaw detected by that system. The fluoroscopic system is a high resolution system, the ultrasonic system avoids detection of minor non-rejectable variation in weld bead geometry and is calibrated to a desired sensitivity level.

10 Claims, 6 Drawing Figures

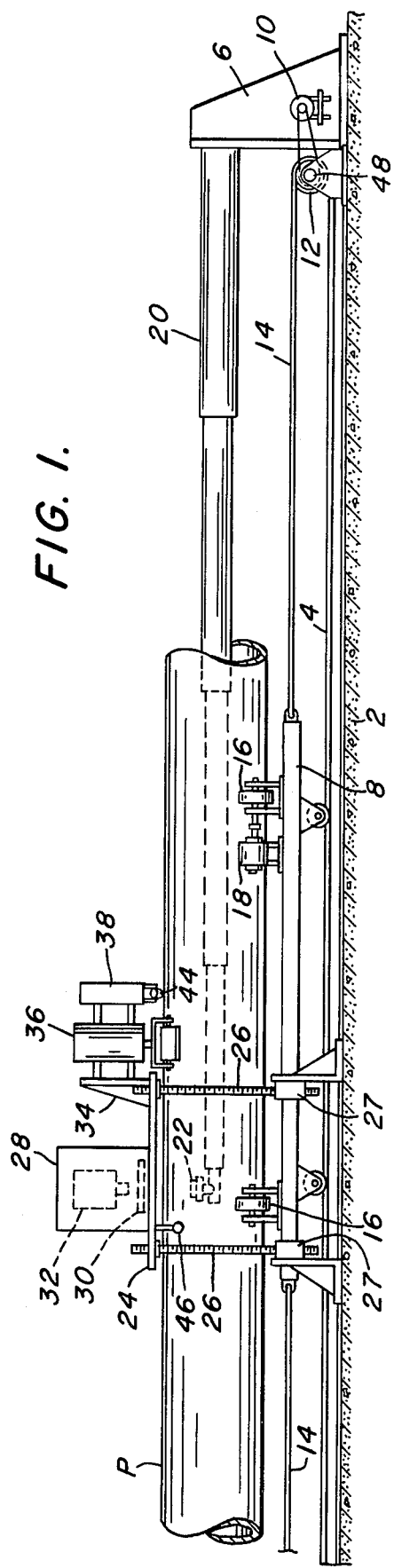
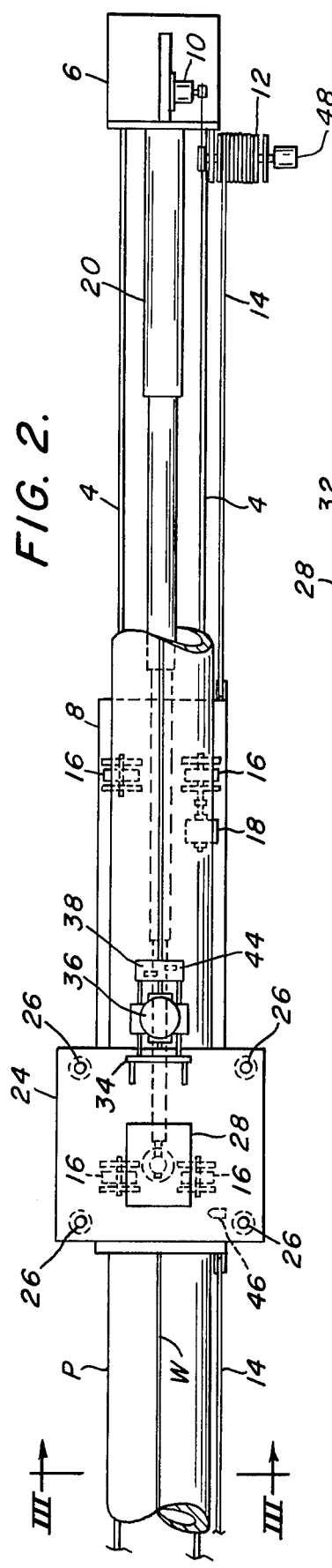
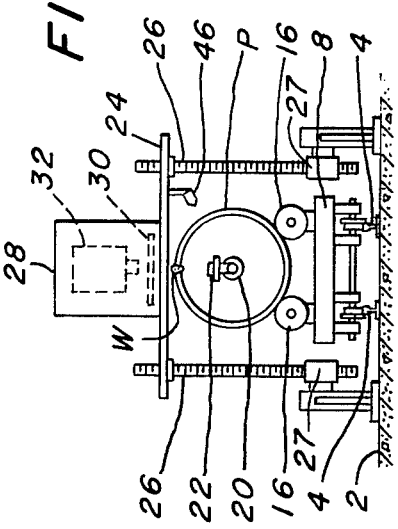
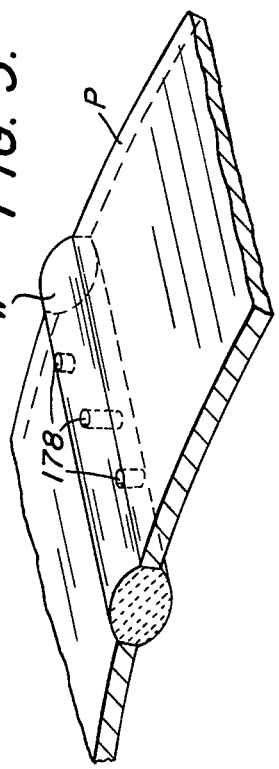

WELD INSPECTION SYSTEM WITH DUAL FLAW DETECTION

This invention relates to the non-destructive inspection of welds and more particularly to a system for detecting flaws in the longitudinal weld of welded pipe using ultrasonic and fluoroscopic techniques.

Weld inspection requirements for large diameter welded pipe have been traditionally established by the American Petroleum Institute (API) specifying ultrasonic and fluoroscopic inspection methods and standards. Intended use of such pipe in Arctic regions has recently inspired different inspection requirements which attempt to force very high detection requirements from ultrasonic inspection systems. These new requirements essentially ignore the useful capabilities of fluoroscopic inspection. Application of such revised inspection and detection requirements result in alarm rates as high as 20% and beyond requiring considerable confirmatory inspection and reinspection. Such reinspection requires additional equipment, manpower and handling, and typically discloses that actual weld imperfection not meeting standards range between 6 and 10 percent.

Most efforts in the past to use radialogical and ultrasonic inspection together have been directed towards the use of one method for confirming the detections of the other method. However, we have found that the reliability of weld inspection can be greatly improved if the ultrasonic method is used for detecting the type of flaws for which it is particularly useful, planar type flaws such as fine cracks, undercuts, incomplete penetration or lack of fusion while the fluoroscopic method is used for detecting the type of flaw for which it is particularly useful, volumetric type flaws such as gas or slag.

In accordance with our invention, a high resolution fluorescent screen system with a high sensitivity-high resolution television system providing a fluoroscopic system capable of meeting known penetrameter specifications and an ultrasonic inspection head which detects weld flaws with insensitivity to minor non-rejectable variations in weld bead geometry provides an ultrasonic system capable of meeting API and other standards for ultrasonic inspection are both used to inspect a weld. The apparatus is arranged for simultaneous inspection by both systems, which share common workpiece handling, control and data handling equipment. The inspection is carried out throughout the length of the pipe by both systems and each system places a mark on the pipe to identify the location along the pipe where the flaw was detected, the mark being distinguishable from a mark placed on the pipe by the other system.

It is therefore an object of our invention to provide a weld inspection system that reliably detects all weld flaws which minimizes overinspection.

Another object is to provide a weld inspection system with one part of the system particularly sensitive to detection of planar type flaws and the other part of the system particularly sensitive to volumetric type flaws.

A further object is to provide an inspection system that marks the location of a flaw location detected by ultrasonic technique distinguishable from the mark of a flaw location detected by a fluoroscopic technique.

Yet another object is to provide an inspection system that counts the number of flaws detected by ultrasonic technique, the number of flaws detected by fluoroscopic technique, and the number of correlated flaws detected by both techniques.

Figure 6:
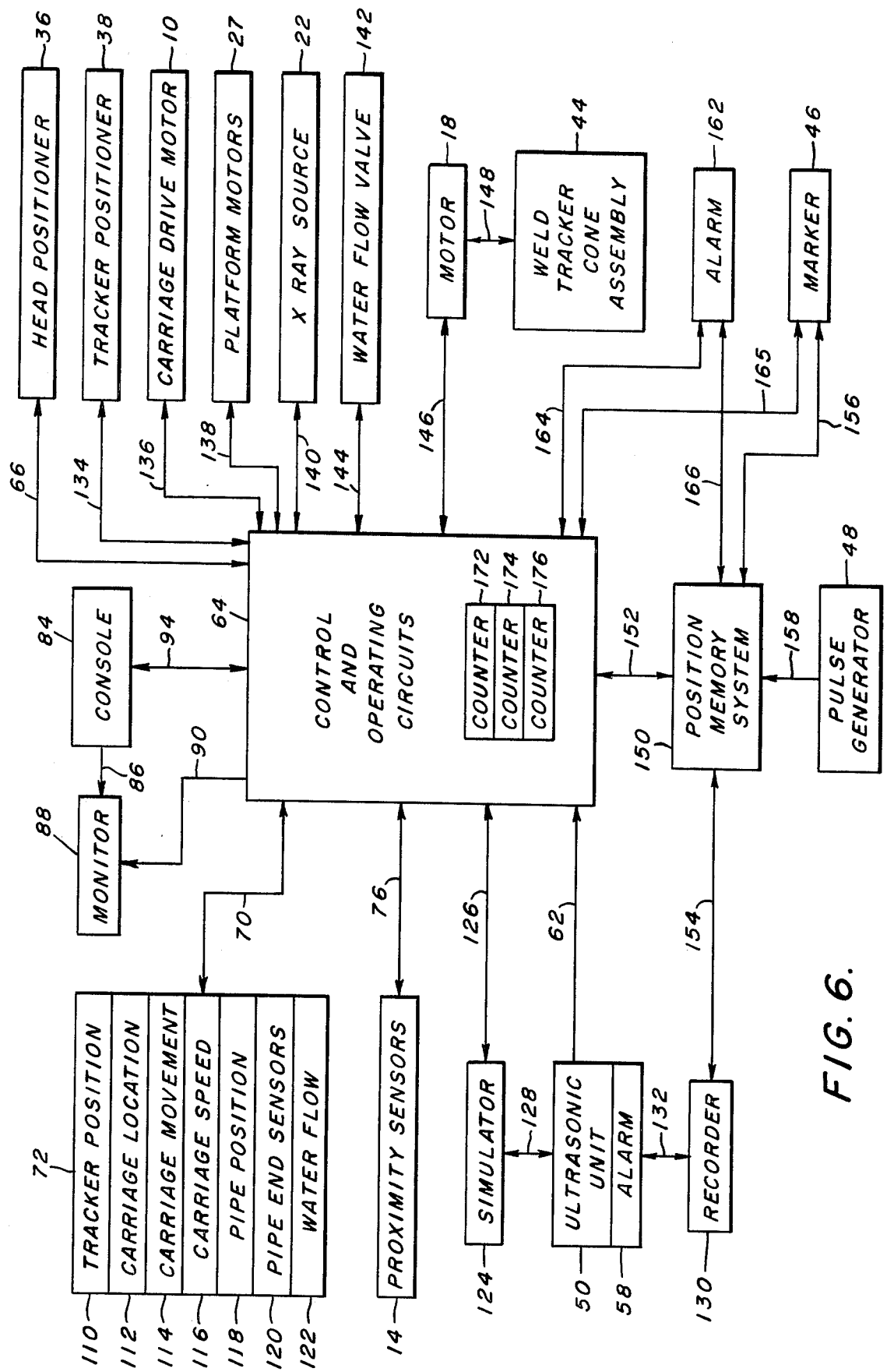

These and other objections will become more apparent after referring to the following specification and drawings in which FIG. 1 is an elevational view of part of the apparatus of our invention, FIG. 2 is a plan view of the apparatus of FIG. 1, FIG. 3 is a partial sectional end view looking along line III—III of FIG. 2, FIG. 4 is a simplified schematic and block diagram of the inspection system of our invention, FIG. 5 is a perspective view of a section of pipe showing calibration holes, and FIG. 6 is a diagramatic sketch showing the functioning of the control and operating circuits of the system.

Referring now to FIGS. 1, 2 and 3, reference numeral 2 indicates a base upon which are mounted the components of the apparatus of our invention. A pair of rails 4 on base 2 extend between a boom support 6 as shown on the right end of rails 6 in FIGS. 1 and 2 and a loading station (not shown) on the other end. A carriage 8 is mounted for movement along rails 4. Carriage 8 is moved by a motor 10 driving a drum 12 around which is wound a cable 14 which passes over a pulley at the loading station and whose ends are attached to carriage 8. Support rollers 16 mounted on carriage 8 support a length of pipe P being inspected. A motor 18 is connected to turn a roller 16 to position a weld W in pipe P for inspection by rotating pipe P. One end of a boom 20 is attached to support 6. A source of x-rays 22, directing radiation vertically from the center line of the pipe P when supported by rollers 16, is mounted on the other end of boom 20.

An inspection platform 24 is located over rails 4 and is supported by four screw jack posts 26. Platform 24 is raised and lowered by motors 27 turning posts 26. A housing 28 is mounted on platform 24. A fluorescent screen 30 and a television camera 32 are mounted inside housing 28. A bracket 34 is mounted on one end of platform 24. An ultrasonic inspection head assembly positioner 36 and a weld tracker assembly positioner 38 are mounted on bracket 34. Attached to the bottom of positioner 36 is a pair of inspection head supporting frames 40 (FIG. 4), one on each side of the weld test position. Each frame has three rollers which rest on the pipe during inspection and each frame has mounted on it on inspection head 42 (FIG. 4) preferably of the type shown in Patsey application Ser. No. 667,770 filed Mar. 17, 1976 and entitled, "Ultrasonic Testing System." Other types of inspection heads in other systems may also be used. Attached to the bottom of positioner 38 is a weld tracker cone assembly 44, which, together with other components described herein, is preferably of the type shown in Schindler application Ser. No. 510,685, filed Sept. 30, 1974 now U.S. Pat. No. 3,970,910 and entitled, "Weld Tracking Mechanism." A marker 46 is mounted on platform 24 adjacent the path of the pipe during inspection. A pulse generator 48 is connected to drum 12.

Referring now to FIG. 4 which shows some of the elements already described, an ultrasonic testing unit 50, such as a Model UM 771 or UM 775 manufactured by Automation Industries, Inc. is mounted in the system operator's control booth at a location convenient for the operator. Unit 50 may include a cathode ray display 52, a multiplexer 54, calibration controls 56, and alarm circuit 58. Unit 50 has a connection 60 to inspection heads 42 and a connection 62 to control and operating circuitry 64. Circuitry 64 has a connection 66 to positioner 36, a connection 68 to marker 46, and a connection 70 to a group of position and status inputs 72 to be described later. A pair of proximity sensors 74 are mounted on frames 40 and have a connection 76 to circuitry 64.

Camera 32 has a connection 78 to a camera control unit 80. Unit 80 is connected to an operator's console 84 in the operator's control booth. Console 84 has a connection 86 to a TV monitor 88. Monitor 88 has a connection 90 to circuitry 64. Console 84 has a connection 94 to circuitry 64, a connection 96 to a fluorographic unit 98. Unit 98 includes a slave monitor 100, an integrator 102 to improve the image, a 35 mm camera 104 and an image storage system 106. The parts enclosed within broken line 108 are all preferably part of a system of the type shown in Green Application Ser. No. 667,925 filed Mar. 17, 1976 and entitled "X-Ray Inspection of Welds", an inspection system particularly adapted to our inspection system. Other types of fluoroscopic inspection systems may also be used.

Referring now to FIG. 6, a reference numberal 64 is a group of conventional logic, sequencing and control circuits for operating the various parts of the inspection apparatus in the manner desired, either automatically, or manually or some combination of manual and automatic operation at the desire of the operator. The inputs 72 include a tracker cone assembly proximity detector 110 for providing a signal indicating the absence or presence of pipe P under assembly 44, a plurality of location sensors 112 at locations along rails 4 for providing signals indicating the absence or presence of carriage 8 at specified locations, a carriage movement sensor 114 for providing a signal indicating whether or not carriage 8 is moving and direction of movement, a carriage speed sensor 116 for providing a signal indicating the speed of movement of carriage 8, pipe position sensors 118 for providing a signal indicating that pipe P is properly placed on rollers 16, pipe end sensors 120 for providing signals indicating the presence or absence of the end of pipe P at specific locations and a water flow sensor 122 for providing a signal to indicate that the flow of couplant water to inspection heads 42 is satisfactory.

An ultrasonic system simulator 124 has a connection 126 to circuits 66 and a connection 128 to ultrasonic unit 50. A two pen-two channel recorder 130 has a connection 132 to unit 50. Weld tracker assembly positioner 38 has a connection 134 to circuitry 64. Motor 10 has a connection 136 to circuitry 64. Platform motors 27 have a connection 138 to circuitry 64. X-ray source 22 has a connection 140 to circuitry 64. An electrically operated water flow valve 142, for turning on and off the couplant water to inspection head 42 has a connection 144 to circuitry 64. Motor 18 has a connection 146 to circuitry 64 and a connection 148 to weld tracker assembly 44.

A position memory system 150 has a connection 152 to circuitry 64, a connection 154 to recorder 130, a connection 156 to market 46, a connection 158 to pulse generator 48, and a connection 166 to alarm 162. Alarm 162 has a connection 164 to circuitry 64. Marker 46 has a connection 165 to circuitry 64. System 150 accepts bidirectional pulses from pulse generator 48 and uses conventional shift register techniques to provide position signals with respect to length of pipe inspected and flaw location. Circuitry 64 includes a video pattern generator for providing a cursor 166 (FIG. 4) on monitor 88 to track an ultrasonic flaw 168 (FIG. 4) under the control of system 150. Circuitry 46 includes a first counter 170, a second counter 172, and a third counter 174.

Before beginning the inspection process, the sensitivity of unit 50 is adjusted so that it will detect a designated type calibration standard. One such standard, API, requires detection of a 1.6 mm hole in the weld. A calibration pipe section, shown partially in FIG. 5 is placed under the inspection head and the calibration control 56 adjusted until the three 1.6 mm holes 178 through the center and each side of the weld are detected at the desired sensitivity level. With all units electrically energized, platofrm 24 rasised, the inspection head assembly raised, the weld tracker assembly raised, and the couplant water flow turned off the system is ready to accept a length of pipe for inspection. A proctective shutter covers x-ray source 22 except when pipe end sensors indicate pipe is over source 22.

As soon as a length of pipe P is loaded on carriage 8 at the loading station, the operator, by selecting the proper control on console 84 starts the automatic inspection sequence. The operator has manual override controls on console 84 with which he may interrupt the automatic process at any time. Carriage 8 moves along rails 4 to the right until pipe end sensors 120 indicate the right end of the pipe, as oriented in FIGS. 1 and 2, has reached source 22. Platform 24 is lowered, the shutters on 22 are opened so that fluoroscopic view is on the screen of monitor 88. As the carriage continues to move, the operator manually controls motor 18 to rotate the pipe to the desired inspection position using the image of the weld W appearing as a band W on the screen of monitor 88 in relation to a mask to select the desired weld position.

When pipe end sensors 120 indicate the left end of the pipe is approaching source 22, inspection heads 42 and weld tracker assembly 44 are lowered onto the pipe, couplant water is turned on and when carriage 8 reaches the limit of travel for inspecting the left end of the pipe, carriage 8 stops and starts moving to the left to begin actual inspection. Position memory system 150 is now activated, keeping a record of increment lengths of pipe inspected as carriage 8 travels along rails 4. The total distance may be shown on the monitor, for example as shown at 180. The operator, through console controls, may also display any desired identification data which may subsequently be recorded by camera 104. The speed of carriage 8 may now be limited to the maximum established by API standards. The weld tracker maintains pipe position and pulse generator 48 provides pulses to system 150 as carriage 8 moves.

Ultrasonic inspection is performed automatically. Multiplexer 54 uses the receiver in one inspection head to check transmission from the other inspection head, a conventional technique. Alarm 58 is initiated when multiplexer 54 determines the sonic coupling check is unsatisfactory. Alarm 58 may be used to light a warning lamp 182 on monitor 88 and make a record on recorder 130. If an ultrasonic flaw is detected by unit 50, a signal is sent to counters 172 and 174, to memory system 150, to alarm 162 and a reocrd made on recorder 130. Alarm 162 may indicate the presence of a flaw either audibly for the operator's benefit or by lighting a lamp 184 at monitor 88 when the flaw indication area is in the field of view of the monitor 88. Since it is not convenient to locate marker 46 at inspection head 42, the flaw signal is held in system 150 until the pipe has moved to a location where the flaw location is at the marker and the signal then activates the marker, preferably a paint spray. The operator may visually confirm the presence of the flaw which appears on cathode ray display 52.

Fluoroscopic inspection is performed visually by the operator watching the weld passing in view on monitor screen 88. Since the sensitivity and resolution system 108 can readily meet the 2% penetrameter standards of API, the operator can readily detect flaws. When a flaw is detected, a record is made with console controls, activating counters 174 and 176 and providing a signal to activate marker 46 at the appropriate time to mark the pipe, preferably a paint spray of a color to distinguish from an ultrasonically detected flaw. The operator may make a record of the flaw by storing the image, 1106, and photographing the image with camera 104. Location data 180 may also be recorded in this manner. The operator may stop the carriage 4 or move it backwards to study flaw details, for example, to compare with standards concerning flaw size and distribution.

When the right end of the pipe on carriage 8 approaches the pipe end sensors, the weld tracker assembly 44 is lifted off the pipe, the couplant water turned off, the inspection heads raised, the platform raised and a shutter closes off the x-ray source 22. When the carriage 8 has moved to the unloading station, the pipe is removed and the system is ready to begin another inspection cycle.

Cathode ray display 52 is preferably located so that it is not readily visible to the operator as he watches monitor 88 so that he may devote full attention to the fluoroscopic visual inspection. However, the video pattern generator and system 150 provides a cursor 166 a bright bar about 25 mm long which tracks an ultrasonically detected flaw 168 across the screen of monitor 88. The flaw may or may not be visible to the operator. This enables the operator to make a record while maintaining the visual fluoroscopic inspection. Counters 172, 174 and 176 provide totals of ultrasonically detected flaws, fluoroscopic detected flaws and flaws detected by both methods. Totals may be accumulated for any desired event, such as for each piece, a production run, a day or a week.

The two inspection systems produce test results that are separate and distinct from each other although some of the flaws detected by one system are also detected by the other system. No attempt is made to force either system to exceed its capacity for reliable and accurate flaw detection.

A careful evaluation of the system indicates that the number of pipes which have unverifiable ultrasonic alarms is about one percent. In addition, the method will reliably detect flaws to meet existing and anticipated inspection standards for large diameter welded pipe.

The system is particularly adaptable to the inspection of the longitudinal weld of a pipe, but may also be used to inspect spiral welds or other welds joining structures that may be inspected with ultrasonic and fluoroscopic techniques.

While one embodiment of my invention has been shown and described, other modifications and other embodiments may be made to our invention with the scope of the following claims.

We claim:

1. A method for inspecting the longitudinal weld in a pipe comprising the steps of
traversing the weld along a path past a pair of adjacent flaw detection systems operating at the same time and located along a path parallel to the longitudinal axis of the pipe, the first system being a fluoroscopic system particularly sensitive to volumetric type flaws and the second system being an ultrasonic system particularly sensitive to planar type flaws,
maintaining the position of the weld with respect to the path along which the systems are located,
placing a mark on the pipe wall location wherever the first system detects a flaw,
placing a mark on the pipe wall location wherever the second system detects a flaw, and
recording the location, as a distance from the end of the length of pipe, of a flaw detected by the first system on one record and a flaw detected by the second system on a second record.

2. A method according to claim 1 which includes the steps of
providing an image of the display on the fluorescent screen of the fluoroscopic system on a television monitor screen and
providing a video pattern on the monitor screen indicative of the location of a flaw detected by the ultrasonic system as the image of the same location passes over the monitor screen.

3. A method according to claim 2 which includes the steps of
counting the number of flaws detected by the first system and
counting the number of flaws detected by the second system.

4. A method according to claim 3 which includes the step of
counting the number of flaws detected by one system which were also detected by the other system.

5. A weld inspection system using dual flaw detection comprising
means for traversing the weld along a path for inspection,
a source of radiation mounted at a first location along the path for directing the radiation through the weld as the weld moves along the path,
means positioned at the first location for converting the radiation passed through the weld onto an image on a television monitor screen,
an ultrasonic inspection head mounted at a second location along said path for directing ultrasonic energy into and receiving ultrasonic energy from the wall of the material adjacent the weld at one side of the weld, and
an ultrasonic inspection unit connected to the ultrasonic inspection head and responsive to ultrasonic energy received from the ultrasonic inspection head for providing an indication of a flaw.

6. Apparatus according to claim 5 in which the weld is a longitudinal weld in a pipe and means for traversing includes
a pair of rails extending along the path,
a carriage mounted for movement on the rails, and
means mounted on said carriage for supporting the pipe for rotation about its longitudinal axis and which also includes means connected to said support means for rotating the pipe to maintain the pipe in position for inspection.

7. Apparatus according to claim 6 which includes a pulse generator connected to said means for traversing, a position memory system connected to the pulse generator, a first marking means mounted at a location along the path responsive to a signal initiated by a view of the television monitor screen for placing a mark on the wall of the pipe, and a second marking means mounted at a location along the path and connected to the position memory system and responsive to an indication of a flaw by the ultrasonic inspection unit for placing a mark on the wall of the pipe.

8. Apparatus according to claim 7 which includes means adjacent the television monitor screen and connected to the ultrasonic inspection unit for providing an indication of a flaw detection by the ultrasonic unit, and means connected to the television monitor screen, the position memory system and the ultrasonic inspection unit for providing a visible identification on the television monitor screen indicative of the location of a flaw detected by the ultrasonic unit as the image of the location passes across the screen.

9. Apparatus according to claim 8 which includes a second ultrasonic inspection head connected to the ultrasonic unit and mounted adjacent the first inspection head on the other side of the weld, means connected to the inspection heads and the inspection unit for checking the sonic coupling between each inspection head and the pipe wall, means connected to the inspection unit for indicating said sonic coupling is in an unsatisfactory condition, and means connected to the ultrasonic unit for recording indications of a flaw.

10. Apparatus according to claim 9 which includes a first counting means conected to the ultrasonic unit and the position memory system for counting indications of a flaw, a second counting means connected to the position memory system for counting the number of signals initiated by the viewer, and a third counting means connected to the first and second counting means for counting entries into the first and second counting means correlated with the same location along the pipe length.

* * * * *

UNITED STATES PATENT OFFICE
CERTIFICATE OF CORRECTION

Patent No. 4,055,989    Dated November 1, 1977

Inventor(s) E. Blair Henry, Jr., John A. Patsey, Ralph G. Rudolph, Donald G. Schindler It is certified that error appears in the above-identified patent and that said Letters Patent are hereby corrected as shown below:

Column 3, line 23, "numberal" should be --numeral--;

Column 4, line 15 "platofrm" should be --platform--;

Column 4, line 63 "reocrd" should be --record--;

Column 5, line 17 "1106" should be --106--;

Column 6, line 15, "as" should be --at--;

Signed and Sealed this

Twenty-eighth Day of February 1978

[SEAL]

Attest:

RUTH C. MASON
Attesting Officer

LUTRELLE F. PARKER
Acting Commissioner of Patents and Trademarks